United States Patent [19]
Parks

[11] Patent Number: 6,133,310
[45] Date of Patent: Oct. 17, 2000

[54] METHOD OF TREATMENT OF ROSACEA

[76] Inventor: L. Dean Parks, 2420 SE. 15th St., Ocala, Fla. 33471

[21] Appl. No.: 09/383,594

[22] Filed: Aug. 26, 1999

[51] Int. Cl.$^7$ .................................................. A61K 31/35
[52] U.S. Cl. ............................................................ 514/453
[58] Field of Search ................................... 514/859, 453, 514/843, 887; 435/105, 119; 424/449, 443, 444

[56] References Cited

U.S. PATENT DOCUMENTS

| | | | |
|---|---|---|---|
| 5,250,422 | 10/1993 | Petuch et al. ............................. | 435/105 |
| 5,332,577 | 7/1994 | Gertner et al. ........................... | 424/449 |
| 5,952,372 | 9/1999 | McDaniel ................................. | 514/453 |

OTHER PUBLICATIONS

Campos et al., Therapy of the Experimental infection . . . , Rev. Inst. Med. Trop. Sao. Paulo, vol. 31/1, pp. 48–52, (1989).

Kitchen L., Case Studies in . . . , American Family Physician, vol. 60/2, pp. 471–474, (Aug. 1999).

*Primary Examiner*—Marianne M. Cintins
*Assistant Examiner*—Vickie Kim
*Attorney, Agent, or Firm*—M. K. Silverman

[57] ABSTRACT

A method of treatment of acne rosacea consists of the application, in the form of either a lotion or a cream, constituting a mixture of a therapeutically effective amount of invermectin in water, in the case of the lotion, and invermectin and a pharmaceutically acceptable carrier, in the case of the cream. Application to the affected area occurs daily for a period of one week and, thereafter, two to four times per month for a period of up to one year.

5 Claims, No Drawings

METHOD OF TREATMENT OF ROSACEA

BACKGROUND OF THE INVENTION

Rosacea, alternatively known as acne rosacea, is a chronic inflammatory eruption of the nose and adjoining flush areas of the face. Rosacea is characterized by erythema, papules, pustules, telangiectasia and, frequently, by hypertrophy of the sebaceous glands.

This disorder of the skin occurs most often in middle-aged women between the ages of thirty and fifty, however, serious cases have been observed in men. Rosacea, in mild form, brings about a slight flushing of the nose and cheeks and, in some cases, the forehead and chin. However, in a severe form, lesions appear which are deep or purplish red and which include a chronic dilation of the superficial capillaries, this constituting the above-referenced telangiectasia. Also, in severe form, inflammatory acneiform pustules are present. In such serious conditions, the eye or eyelids may become affected. Another acute form of rosacea is known as granulomatous rosacea and, as such, is considered to be a distinctive form of the papular aspect of the disease. Therein, discreet pustules appear as yellowish brown nodules and as epithelioid cell granulomatous.

The etiology of rosacea is not fully known, however, at least four factors or co-factors have been suggested.

The first of these is endocrine in that the disease occurs most frequently in women between the ages of thirty and fifty. As such, one definite type of rosacea is believed to have a hormonal basis.

A second factor is vasomotor lability, believed to have some connection with menopause, which brings about an impairment of normal or consistent flow of blood to the face and its capillaries. Therein, excessive flow of blood to the face, i.e., the well-known "hot flashes" of menopause, are believed to constitute a factor in the disease and its pathogenesis. More particularly, it has been proven that increased skin temperature, as occurs in facial flushing, increases susceptibility to the condition.

Rosacea has also been observed as a side effect or immune response to the use of certain cortisone products, which can bring about a severe form of the condition.

Finally, pathology analysis of the expressed contents of inflamed pustule follicle of the nose in acute rosacea has demonstrated the existence of demodices, which is a signature of the ectoparasite demodex folliculorum. Accordingly, in such cases, a specific external pathogenic factor is evident. This factor is not present in other forms of acne, e.g., acne vulgaris.

After contraction of rosacea, its histology will vary in accordance with the stages of the disorder. Typically, there is a disorganization of the upper dermal connective tissue with edema, disruption of fibers, and often severe elastosis. The inflammatory phase of the disease is marked by the presence of inter- and intra-cellular disorganization.

In the prior art, the treatment of choice has been long-term oral administration of tetracycline on a minimum maintenance dose basis. However, studies have shown that this treatment is only suppressive, not curative. Further, metronidazole has been shown to be as effective as tetracycline, however, it is not as safe when given on a long-term basis. Metronidazole cream, marketed under the mark METROGEL, appears to be safer than the oral forms of metronidazole.

Other agents, for example, isotretinoin, sold under the mark ACCUTANE, produce immediate improvement, however, relapse within a few weeks is typical. The topical antibiotic erythromycin is now used on a long-term daily basis in the management of rosacea. However, as may be appreciated from the above, rosacea has proven to be a recalcitrant condition. Where the menopausal factor is involved, treatment with estrogens has been found to be of value.

Another topical therapy, which is useful in patients that can tolerate it, is benzoyl peroxide gel. However, irritation and burning are common side effects of the use of benzoyl peroxide.

From the above, it may be appreciated that the study and treatment of rosacea has been a long-time concern of the medical community. For example, about 1,000 medical papers have been published on the subject. In addition, approximately 30 U.S. patents exist which are directed to methods or medicinals for use in the treatment of acne rosacea. Such patents which are directed to topical preparations for such treatment are U.S. Pat. No. 4,133,983 (1979) to Spangle, entitled Topical Treatment of Skin Diseases; U.S. Pat. No. 5,569,651 (1996) to Garrison, entitled Gentle Anti-Acne Composition; U.S. Pat. No. 5,654,013 (1997) to Taylor, entitled Method for Treating Rosacea; and U.S. Pat. No. 5,744,156 (1998) to Lacharriere, entitled Use of Substance P Antagonist for the Treatment of Skin Reddening of Neurogenic Origin.

Among the above referenced 1000 medical papers and 30 United States patents, no reference teaches or suggests the utility of the composition invermectin in the treatment of acne rosacea or of any other form of acne. Invermectin itself has, historically, been a product of Merck & Co., Inc., Rahway, N.J. and, for the most part, has been used in veterinary applications for the treatment of endoparasitic conditions in animals. However, some medical papers suggest a topical use of invermectin in humans in the treatment of dermatologic manifestations of endoparasitic conditions such as myiasis and onchocerciasis. These conditions bear no etiologic or histologic connection to acne rosacea or any other form of acne. Demodex, referred above, is caused by a near microscopic ectoparasite, not a macroscopic endoparasite.

Invermectin is a part of a larger chemical family known as the nitro-5-imidazoles which, alternatively, has been termed the 13-deoxy invermectin aglycones. The nitro-5-imidazole family of molecules includes invermectin, ivermectin, avermectin, moxidecion and various derivatives thereof.

The present invention thereby relates to a method of treatment of rosacea and a new use of invermectin in such treatment.

SUMMARY OF THE INVENTION

The instant constitutes a method of treatment of acne rosacea consisting of the application, in the form of either a lotion or a cream, comprising a mixture of a therapeutically effective amount of invermectin in water, in the case of the lotion, and invermectin and a pharmaceutically acceptable carrier, in the case of the cream. Application to the affected area occurs daily for a period of one week and, thereafter, two to four times per month for a period of up to one year.

It is an object of the invention to provide a curative topical therapy for the treatment of acne rosacea.

It is another object to provide a generalized use of the nitro-5-imidodazole family of molecules for the treatment of acne rosacea.

The above and yet further objects and advantages of the present invention will become apparent from the hereinafter set forth Detailed Description of the Invention and claims appended herewith.

DETAILED DESCRIPTION OF THE INVENTION

The inventive topical use of invermectin in the treatment of rosacea entails the use of a therapeutically effective quantity of an invermectin, which is available as a paste, paste with water sufficient to form a lotion having a concentration of at least 750 mcg invermectin per milliliter.

Alternatively, a cream of invermectin may be formed, this in combination with a pharmaceutically acceptable carrier such as propylene glycol, sodium lauryl sulfate, xanthan gum or combinations thereof.

The lotion or cream is then applied on a daily basis for seven days and, thereafter, two to four times per month to the affected area. Thereafter, it is advisable to make application of the lotion or cream once a month as a prophylaxis against recurrence of the condition.

While little is known of the mechanism of action of invermectin upon the skin, it is believed that sebaceous glands, which exist in almost every follicule of human skin, are quieted or in some fashion relaxed by the effect of invermectin thereon. Also, invermectin is believed to have a de-sensitizing effect on the skin and, thereby, is of value with respect to autoimmune factors associated with the condition. Further, the quieting and de-sensitizing aspects of invermectin are believed to subdue vasomotor liability, thereby cooling the face and reducing swelling associated with capillary stress.

Over a period of experimental testing of about five years upon about 100 patients in my practice in Ormond Beach, Fla., I have found results of the above method to be both safe and remarkably effective in treatment of this otherwise stubborn condition of acne and, further, I have seen no recurrence of the condition where treatment has occurred in the fashion set forth above. Further, none of the side effects, such as irritation or burning, associated with such prior art medication as benzoyl peroxide have appeared. In addition, in my use of the above described invermectin lotion and cream, I have not encountered any immune response from patients so treated as, occasionally, is the case with antibiotics such as erythromycin and tetracycline.

Accordingly, I believe that an effective and almost universally safe method has been identified for the treatment and cure of acne rosacea.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

Having thus described my invention, what I claim as new, useful and non-obvious and, accordingly, secure by Letters Patent of the United States is:

1. A method of treatment of acne rosacea, consisting of the steps of:

(a) mixing a therapeutically effective amount of invermectin with water to thereby form a lotion;

(b) applying said lotion daily to an affected area for a period of about seven days; and (c) repeating such application two to four times a month for a period of several months; and, optionally, repeating application of said lotion about once a month thereafter.

2. The method as recited in claim 1, in which said therapeutically effective amount of invemectin comprises a concentration of at least 750 mcg/ml.

3. A method of treatment of rosacea, consisting of the steps of:

(a) mixing a therapeutically effective amount of invermectin with a pharmaceutically acceptable carrier to thereby form a cream; applying said cream daily to an affected area for a period of about seven days; and (b) repeating such application two to four times a month for a period of several months; and, optionally, repeating application of said cream about once a month thereafter.

4. The method as recited in claim 3 in which said therapeutically effective amount of invermectin comprise a concentration of at least 750 mcg/cc within said cream.

5. The method as recited in claim 4 in which said pharmaceutically acceptable carrier is selected from the group of carriers consisting of propylene glycol, sodium lauryl sulfate, xanthum gum, or combinations thereof.

* * * * *